US00PP27966P2

(12) United States Plant Patent
Williams

(10) Patent No.: US PP27,966 P2
(45) Date of Patent: May 2, 2017

(54) ***COLOCASIA* PLANT NAMED 'BLACK SAPPHIRE GECKO'**

(50) Latin Name: ***Colocasia* hybrid**
Varietal Denomination: Black Sapphire Gecko

(71) Applicant: Brian Paul Williams, Louisville, KY (US)

(72) Inventor: Brian Paul Williams, Louisville, KY (US)

(73) Assignee: Brian's Botanicals, Louisville, KY (US)

( * ) Notice: Subject to any disclaimer, the term of this patent is extended or adjusted under 35 U.S.C. 154(b) by 73 days.

(21) Appl. No.: 14/545,492

(22) Filed: May 12, 2015

(51) Int. Cl.
*A01H 5/12* (2006.01)

(52) U.S. Cl.
USPC ..... Plt./373

(58) Field of Classification Search
USPC ..... Plt./373, 226, 263.1, 258
See application file for complete search history.

(56) References Cited

PUBLICATIONS

Brians Botanicals retrieved on Sep. 8, 2016, retrieved from the Internet at <http://briansbotanicals.us/index.php/plant-catalog/colocasia/colocasia-black-sapphire-gecko-ppaf-detail> 1 p.*
Hummert International Plants & Cuttings 2015 retrieved on Sep. 8, 2016, retrieved from the Internet at <http://www.hummert.com/_uploads/default/pdfs/PC_2015_Web.pdf> p. 48.*
Plant Nouveau retrieved on Sep. 8, 2016, retrieved from the Internet at <http://plantsnouveau.com/plant/colocasia-black-sapphire-gecko/> 2 pp.*

* cited by examiner

*Primary Examiner* — June Hwu
(74) *Attorney, Agent, or Firm* — Penny J. Aguirre

(57) ABSTRACT

A new cultivar of *Colocasia* plant named 'Black Sapphire Gecko', that is characterized by its clump forming, large plant habit growing up to 1.8 m in height, its leaves that are dark purple-black in color with a reflective sheen on the upper surface and maroon in color on the lower surface, its petioles that are dark maroon in color, its healthy root system that is cold hardy up to U.S.D.A. Zone 7, and its production of large tubers as it ages.

2 Drawing Sheets

Botanical classification: *Colocasia* hybrid.
Cultivar designation: 'Black Sapphire Gecko'.

BACKGROUND OF THE INVENTION

The present invention, *Colocasia* 'Black Sapphire Gecko', relates to a new and distinct interspecific hybrid of *Colocasia*, hereinafter referred to by its cultivar name, 'Black Sapphire Gecko'. 'Black Sapphire Gecko' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Colocasia* plants with colorful foliage and that are well suited for landscape or containers. 'Black Sapphire Gecko' arose from a cross make in June of 2011 between unnamed proprietary *Colocasia* hybrid plants (not patented) from the Inventor's breeding program as the female and male parents. 'Black Sapphire Gecko' was selected as a single unique plant in June of 2013 from amongst the seedlings derived from the above cross.

Asexual propagation of the new cultivar was first accomplished by in vitro propagation using meristem tissue under the direction of the Inventor in Eustis, Fla. in March of 2014. Asexual propagation by in vitro propagation has shown that the characteristics of the new cultivar are stable and reproduced true to type in successive generations

SUMMARY OF THE INVENTION

The following traits have been repeatedly observed and represent the characteristics of the new cultivar. These attributes in combination distinguish 'Black Sapphire Gecko' as a new and unique cultivar of *Colocasia*.

1. 'Black Sapphire Gecko' exhibits a clump forming, large plant habit growing up to 1.8 m in height.
2. 'Black Sapphire Gecko' exhibits large leaves that are dark purple-black in color with a reflective sheen on the upper surface and maroon in color on the lower surface.
3. 'Black Sapphire Gecko' exhibits petioles that are dark maroon in color.
4. 'Black Sapphire Gecko' exhibits a healthy root system that is cold hardy up to U.S.D.A. zone 7.
5. 'Black Sapphire Gecko' exhibits the production of large tubers as it ages.

The female parent of 'Black Sapphire Gecko', differs from 'Black Sapphire Gecko' in being shorter in height, in having leaves with dull surfaces (no sheen), in having small running tubers, and in having petioles that are brownish-black in color. The male parent of 'Black Sapphire Gecko' differs from 'Black Sapphire Gecko' in being shorter in height and in having leaves that are brown to dark brown in color on both surfaces. 'Black Sapphire Gecko' can be most closely compared to the *Colocasia* cultivars 'Black Magic' (not patented) and 'Mammoth' (not patented). 'Black Magic' differs from 'Black Sapphire Gecko' in being shorter in height, in having leaves with dull surfaces, and in having leaf lower surfaces that are gray in color. 'Mammoth' differs from 'Black Sapphire Gecko' in being taller in overall height and in having leaves and petioles that are green in color.

BRIEF DESCRIPTION OF THE DRAWINGS

The accompanying colored photographs illustrate the overall appearance and distinct characteristics of the new

*Colocasia*, 'Black Sapphire Gecko'. The photographs were taken of two year-old plants as grown outdoors, in full sun, under two mm poly in Louisville, Ky.

Figure 1:
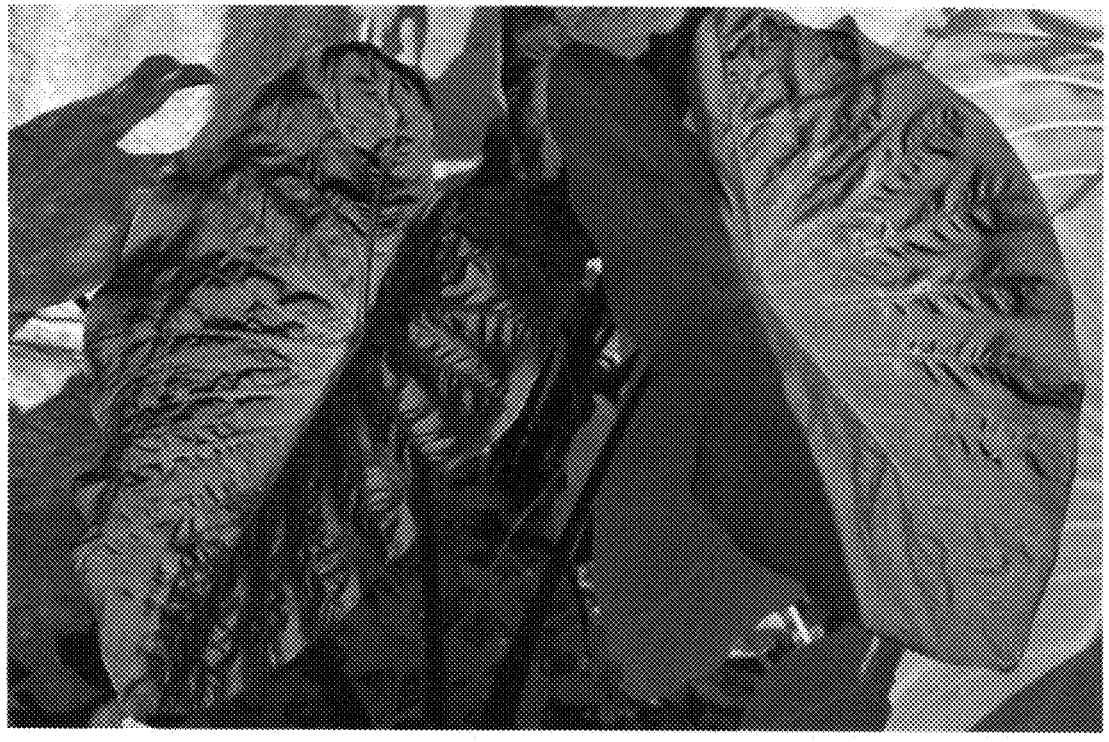

The photograph in FIG. 1 provides an overall view of the mature foliage and plant habit of 'Black Sapphire Gecko'.

Figure 2:
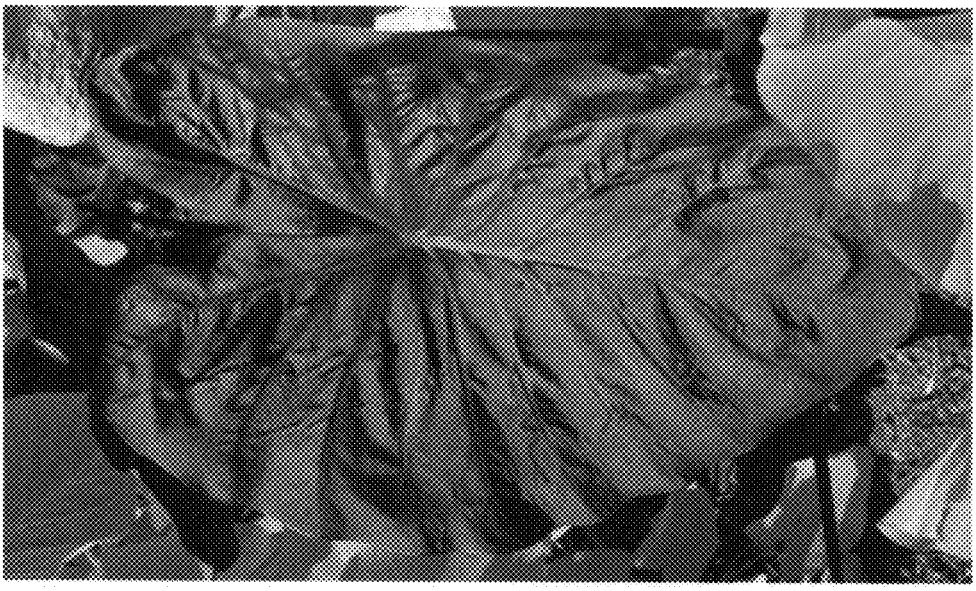

The photograph in FIG. 2 provides a close-up view of the upper surface of a leaf of 'Black Sapphire Gecko'.

Figure 3:
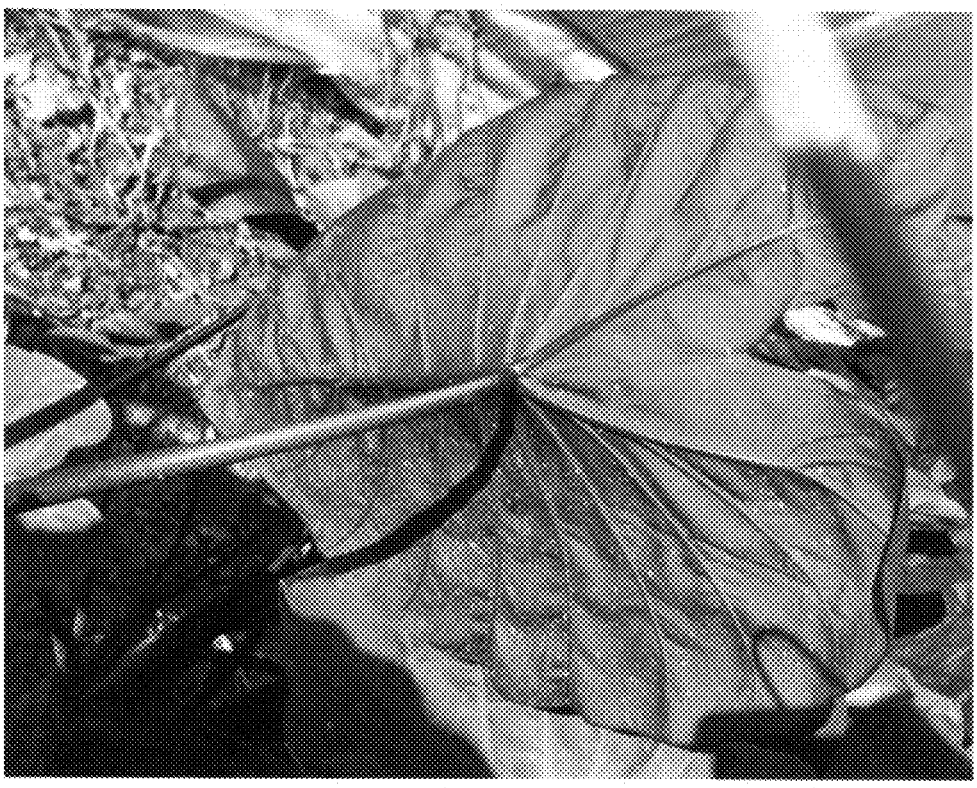

The photograph in FIG. 3 provides a close-up view of the lower surface of a leaf of 'Black Sapphire Gecko'.

The colors in the photographs are as close as possible with the digital photography techniques available, the color values cited in the detailed botanical description accurately describe the colors of the new *Colocasia*.

DETAILED BOTANICAL DESCRIPTION OF THE PLANT

The following is a detailed description of three year-old plants of the new cultivar plants as grown outdoors, in full sun, under two mm poly in Louisville, Ky. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—August to September in Kentucky.

*Plant type.*—Tropical perennial herb.

*Plant habit.*—Upright, stemless, clump forming.

*Height and spread.*—Reaches up to 1.8 m in height and 1.2 m in width.

*Cold hardiness.*—At least to U.S.D.A. Zone 7.

*Diseases and pests.*—No resistance or susceptibility to diseases and pests has been observed.

*Roots.*—Fleshy, 183D in color.

*Propagation type.*—In vitro propagation.

*Growth rate.*—Vigorous.

*Stem description.*—Stemless, can produce large tubers with age; formed at the base of the petioles with age, about 15 to 23 cm in diameter and 8 to 10 cm in height on a 2 year-old plant, comprised of petiole scales, surface is rough and paper-like, color is a blend of N199B and N199D.

Foliage description:

*Leaf shape.*—Ovate.

*Leaf division.*—Single.

*Leaf base.*—Cordate.

*Leaf apex.*—Acute to rounded.

*Leaf venation.*—Pinnate, conspicuous but not prominent.

*Leaf margins.*—Entire and slightly undulate.

*Leaf attachment.*—Petiolate.

*Leaf arrangement.*—Single.

*Leaf surface.*—Upper surface and lower surface; rugose, coriaceous, and glabrous.

*Leaf orientation.*—Held downward.

*Leaf color.*—Young foliage: upper surface; N186A and lower surface 182A with veins 183D; mature foliage upper surface; 202A with veins 202B, mature foliage lower 182A with veins 183D.

*Leaf size.*—An average of 0.7 m in length and 35.56 cm in width.

*Leaf sinus depth.*—Average of 7.62 cm.

*Petioles.*—Held erect to semi-erect, an average of 38 cm in length and 4 mm in distal diameter and 15 mm in proximal diameter, glaucescent surface, color; N186A, the basal sheath portion is triangular in shape, N186A in color on outer surface and 189A in color on the inner surface, 5 cm in diameter and 8 cm in length, glabrous on both surfaces and glossy surface on the outer surface.

Inflorescence description:

*Inflorescence type.*—Spadix surrounded by a spathe, male portion held above female portion, only female flowers are developed.

*Inflorescence size.*—An average of 18 cm in length and 1.7 cm in width.

*Inflorescence bud.*—Linear to slightly narrow lanceolate in shape, an average of 12 cm in length and 3 cm in width.

*Flower fragrance.*—None.

*Lastingness of inflorescence.*—Inflorescence blooms intermittently during the bloom period, individual flowers last about 2 to 3 weeks.

*Inflorescence/flower quantity.*—An average of 160 female flowers sessile to spadix, sessile male flowers are undeveloped.

*Spathe.*—Hooded, bract, subtending spadix, an average of 15.5 cm in length and 3 cm in width, entire margin, bottom portion; elliptic in shape, an average of 3.1 cm in length and 3.2 cm in width, apex fused to upper portion, truncate base, upper portion (hood); oval in shape, an average of 15 cm in length and 2.8 cm in width, acute apex, upper and lower portion inner and outer surface; coriaceous and smooth, color; upper and lower portion outer surface 187A to 187C and inner surface a mix of 186A and 150C to 150D, especially towards the base.

*Spadix.*—Male portion above female zone, upright linear in shape (phallus like), apex narrowly pointed, an average of 5.5 cm in length and 6 mm in width, a mix of N187A to N187B and N155C towards the base in color, female portion; ovate in shape, an average of 2 cm in length and 8 mm in width, a mix of NN155A and N187A in color.

*Peduncle.*—Grows from base of plant, triangular to rounded in shape, an average of 9 cm in length and 6.5 mm in diameter, durable and strong, a blend of 187A to 187C and N187A in color, coriaceous, glabrous, and smooth surface.

Reproductive organs:

*Gynoecium.*—1 pistil with an average of 3 to 5 carpels, N187A to N187B in color, ovary is round in shape, full of many minute ovules, and 142C in color.

*Androecium.*—Undeveloped.

Fruit and seed: Sterile.

It is claimed:

1. A new and distinct cultivar of *Colocasia* plant named 'Black Sapphire Gecko' as herein illustrated and described.

* * * * *